US010739343B2

(12) United States Patent
Fleischer et al.

(10) Patent No.: US 10,739,343 B2
(45) Date of Patent: Aug. 11, 2020

(54) STRIP FOR MONITORING ANALYTE CONCENTRATIONS

(71) Applicant: Biostrip ApS, Risskov (DK)

(72) Inventors: Jesper Fleischer, Højbjerg (DK); Michael Hasenkam, Harlev (DK); Niels E. Magnusson, Lystrup (DK); Hans Nygaard, Rønde (DK)

(73) Assignee: Biostrip ApS

( * ) Notice: Subject to any disclaimer, the term of this patent is extended or adjusted under 35 U.S.C. 154(b) by 170 days.

(21) Appl. No.: 15/998,706

(22) Filed: Aug. 16, 2018

(65) Prior Publication Data

US 2019/0094217 A1 Mar. 28, 2019

Related U.S. Application Data

(62) Division of application No. 14/785,746, filed as application No. PCT/EP2014/058473 on Apr. 25, 2014, now Pat. No. 10,094,824.

(30) Foreign Application Priority Data

Apr. 25, 2013 (EP) ..................................... 13165411

(51) Int. Cl.
*G01N 33/558* (2006.01)
*G01N 27/327* (2006.01)
*G01N 27/403* (2006.01)
(52) U.S. Cl.
CPC ....... *G01N 33/558* (2013.01); *G01N 27/3275* (2013.01); *G01N 27/403* (2013.01)

(58) Field of Classification Search
CPC . G01N 33/558; G01N 27/3275; G01N 27/403
See application file for complete search history.

(56) References Cited

U.S. PATENT DOCUMENTS

2002/0076690 A1* 6/2002 Miles ................. G01N 33/5438
435/5
2005/0069905 A1* 3/2005 Myerholtz ......... G01N 33/5438
435/6.19

(Continued)

Primary Examiner — Melanie Brown
(74) Attorney, Agent, or Firm — Dinsmore & Shohl LLP; Weston R. Gould

(57) ABSTRACT

The present invention concerns a device for measuring the concentration of analytes in liquid samples such as bodily samples. The device comprises an application zone, to which a sample can be applied, and which contains a specific molecule capable of specifically binding the analyte of interest, said specific molecule being conjugated to a reporter which can give rise to variations in impedance. The resulting complex migrates by capillarity and enters a detection zone, on which another molecule capable of specifically binding the analyte of interest is immobilised. The concentration of reporter molecules in the detection zone is proportional with the concentration of analyte in the sample, and variations in concentration of reporter molecules yield a measurable change in electrical properties such as a change in impedance and/or capacitance which can be correlated to the concentration of analyte. The device is useful for monitoring concentrations of analytes that are biological markers for bacterial, viral or fungal infections, diseases or medical conditions, or their severity, in animals such as humans, farm animals, fish and pets, and in plants.

17 Claims, 6 Drawing Sheets

(56) References Cited

U.S. PATENT DOCUMENTS

| | | | | |
|---|---|---|---|---|
| 2010/0120016 A1* | 5/2010 | Li | ............................ | C12Q 1/04 |
| | | | | 435/5 |
| 2010/0297683 A1* | 11/2010 | Krause | ................... | C12Q 1/001 |
| | | | | 435/23 |
| 2013/0029872 A1* | 1/2013 | Ishige | ................ | G01N 27/3275 |
| | | | | 506/9 |
| 2013/0161190 A1* | 6/2013 | Ewart | ............... | B01L 3/502715 |
| | | | | 204/403.03 |
| 2014/0323350 A1* | 10/2014 | Nguyen | ............. | G01N 33/5438 |
| | | | | 506/9 |

* cited by examiner

STRIP FOR MONITORING ANALYTE CONCENTRATIONS

CROSS REFERENCE TO RELATED APPLICATIONS

This application is a divisional of U.S. patent application Ser. No. 14/785,746 filed Oct. 20, 2015, which is a U.S. National Stage of PCT/EP2014/058473 filed Apr. 25, 2014, and claims priority to European Patent Application No: 13165411.3 filed Apr. 25, 2013, the entire, contents of each of which are incorporated herein by reference.

FIELD OF INVENTION

The present invention relates to a device for measuring the concentration of analytes in a liquid sample by measuring the induced changes in electrical properties in a detection zone. The said device is particularly useful for determining the concentration of biological markers in bodily samples, such as blood, urine or interstitial fluid samples, plant samples or environmental samples, wherein the said biological markers are characteristic of an infection, a disease or medical condition, or the severity thereof. The device does not require any laboratory setting, and as such is particularly useful for point-of-care monitoring or home monitoring.

BACKGROUND OF INVENTION

As life expectancy increases, chronic diseases are now the biggest cause of death and disability worldwide—including cardiovascular diseases, cancer, diabetes, obesity and chronic respiratory diseases—and account for an estimated 86% of deaths and 77% of the disease burden in the European Region, as measured by disability-adjusted life-years. This development has brought about a fundamental shift in health systems and health care and thus in the roles of patients. The focus on patient self-care practices has grown substantially, and much care and treatment takes place at home, leaving patients and family with greater responsibility for their own health. Patient empowerment is supported by the World Health Organization, but requires that patients are trained to monitor their own health. Patient empowerment has the potential of being very beneficial for society. An expected consequence is the reduction of healthcare costs. The chronic patients self-monitoring their condition at home can reduce their own stress, and avoid unnecessary visits at a medical practice when the disease is under control, thus allowing practitioners to spend more time and resources on acutely ill patients.

A number of monitoring devices exist that allow chronic patients to monitor their condition at home: devices for measuring blood pressure for patients with hypertension, glycaemia monitors for patients with type 2 diabetes, cholesterol monitors, and blood coagulation monitors are some examples. However, with the increasing demand for patient empowerment, more devices are needed to measure a range of additional factors involved in other conditions.

SUMMARY OF INVENTION

The present invention relates to a device allowing a quantitative measurement of the concentration of analytes in a biological sample, said device being connected to a reader providing a direct output. The device comprises i) an application zone, to which a sample can be applied, and which comprises a first set of molecules that specifically bind the analytes of interest, said molecules being conjugated to a reporter such as a colloidal metal; ii) one or more detection zones, which can be on a strip consisting of blotting paper and a membrane; said detection zones consisting of areas of the membrane to which a second set of molecules are immobilised that specifically bind the analytes of interest; these molecules can be different from or identical to the first set of specific molecules comprised in the application zone; iii) the application and the one or several detection zones communicate in such a way that the analytes can migrate from the application zone to the one or several detection zones. Upon application of the sample to the application zone, the analytes bind to the specific molecules conjugated to a reporter. When the complexes consisting of the analytes and the reporter-conjugated molecules migrate to the detection zone, the specific molecules immobilized on the detection zone bind the analytes, thereby retaining the reporter-conjugated molecules in the respective detection zones. The increase in concentration of reporter-conjugated molecules leads to and induces detectable changes in electrical properties of the detection zones. Induced changes in electrical properties are in a preferred embodiment changes in the impedance and/or capacitance. Measuring changes in the impedance and/or capacitance can therefore be used to determine the concentration of analyte in the sample, The use of impedance and/or capacitance measurements over a range of frequencies provides a more specific method for measuring the concentration of analyte than similar methods where resistance is measured to determine the concentration of analyte (Lei 2011, Micro and Nano Letters, Vol. 6, Iss. 3, p. 157-160).

The present invention is relevant for monitoring of diseases in mammals, such as humans, cattle, pets, as well as monitoring of disease in plants or animals such as poultry, fish and birds, or assessing environmental samples. The present invention provides a rapid and easy to handle disease monitoring method. It regards all diseases with at least one specific biological marker which can be found in bodily samples originating from animals (such as humans, pets and farm animals, e.g. cattle, poultry, horses) and plants. The invention is particularly well suited for point-of-care or home-monitoring.

Definitions

Analyte

By analyte is understood any component, substance or chemical or biochemical constituent that is of interest. Within the scope of the invention are molecules, including macromolecules, comprised in liquid samples, including bodily samples, such as antigens, proteins, enzymes, peptides, polysaccharides, oligosaccharides, hormones, including growth hormones. Of particular interest are analytes that are biological markers for a disease or a medical condition.

Antibody (Monoclonal, Polyclonal)

Immunoglobulin molecules and active portions of immunoglobulin molecules. Antibodies are for example intact immunoglobulin molecules or fragments thereof retaining the immunologic activity. The term antibody is used herein in the broadest sense and covers monoclonal antibodies (including full length monoclonal antibodies), polyclonal antibodies, multispecific antibodies (e.g., bispecific antibodies), and antibody fragments so long as they exhibit the desired binding specificity.

Anti-dsDNA Antibodies

Anti-dsDNA antibodies are a group of anti-nuclear antibodies and their target antigen is double stranded DNA. Blood tests such as enzyme-linked immunosorbent assay (ELISA) and immunofluorescence are routinely performed to detect anti-dsDNA antibodies in diagnostic laboratories. They are highly diagnostic of systemic lupus erythematosus (SLE). Anti-dsDNA antibodies are highly specific for SLE, and are therefore used in the diagnosis of SLE. Higher titres of anti-dsDNA antibodies are more suggestive of SLE and lower titres can be found in people without the disease.

Anti-Nuclear Antibodies (ANAs)

Anti-nuclear antibodies (ANAs) also known as anti-nuclear factor or ANF) are autoantibodies that bind to contents of the cell nucleus. In normal individuals, the immune system produces antibodies to foreign proteins (antigens) but not to human proteins (autoantigens). In some individuals, antibodies to human antigens are produced. There are many subtypes of ANAs such as anti-Ro antibodies, anti-La antibodies, anti-Sm antibodies, anti-nRNP antibodies, anti-Scl-70 antibodies, anti-dsDNA antibodies, anti-histone antibodies, antibodies to nuclear pore complexes, anti-centromere antibodies and anti-sp100 antibodies. Each of these antibody subtypes binds to different proteins or protein complexes within the nucleus. They are found in many disorders including autoimmunity, cancer and infections, with different prevalences of antibodies depending on the condition. This allows the use of ANAs in the diagnosis of some autoimmune disorders, including systemic lupus erythematosus, Sjögren's syndrome, Scleroderma, polymyositis, dermatomyositis, autoimmune hepatitis and drug-induced lupus.

Antigen

The term antigen designates the compound targeted by an antibody. Antigens are often proteins, polysaccharides or fragments thereof, and can be combined to lipids and nucleic acid fragments. The term antigen is used herein in the broadest sense as any substance that can cause the production of an antibody in an organism.

Application Zone

The term application zone refers to the part of the device to which a sample is applied. The application zone is such that it allows application of a liquid sample, such as, but not limited to, a sample of blood, urine or interstitial fluid. In a preferred embodiment of the present invention, the application zone is located on a strip and comprises blotting paper and a membrane. In another aspect, the application zone consists of or comprise a recess. The application zone may comprise a molecule which is not immobilised and which is capable of binding specifically the analyte of interest. Application of the sample to the application zone allows binding of this specific molecule to the analyte. The application zone can contain several specific molecules, each capable of binding a different analyte.

Biological Markers

By biological marker is understood any analyte which is characteristic of a biological condition. Of particular interest are biological markers that characterize a disease or a medical condition as defined above. Biological markers can be of various natures and sizes. Any biological marker which can be bound specifically either by at least two different molecules or by one molecule capable of binding the biological marker in at least two different sites is within the scope of the invention. For example, a protein which can be bound by two different proteins is within the scope of the invention. Another example is a protein which can be bound simultaneously by a single other protein in two distinct sites. Another example is a protein which exists in a multimeric form, such as dimeric form, in which one monomer can be specifically bound by one protein such as an antibody, and the other monomer(s) can be specifically bound by another protein such as an antibody.

The C-reactive protein (CRP), the tumor factor p53 and the rheumatoid factor (RF) are biological markers of particular interest for the present invention.

Particular embodiments of the invention include but are not limited to the following biological marker/specifically-binding molecule conjugates: protein/protein, enzyme/substrate, antigen/antibody, protein/vitamin.

Bodily Samples

The term bodily samples is used herein in the broadest sense of the term as referring to samples taken from an organism. This organism may be the body of an animal, e.g. humans, farm animals, fish, or the organism may be a plant.

Conjugate Pad

The conjugate pad disclosed herein is made of a highly absorbent type of paper or other material, which is capable of absorbing liquids such as bodily samples. The pad often consists of or comprises superclean cotton, but any paper capable of absorbing liquids is envisioned. Blotting paper for immobilisation of antibodies comprise or consist of either nitrocellulose or polyvinylidene fluoride (PVDF) membranes having high, non-specific binding affinity for amino acids.

C-Reactive Protein (CRP)

The C-reactive protein (CRP) is an acute-phase protein synthesised in the liver and found in the blood. Its levels rise in response to inflammation. CRP binds phosphocholine in damaged cells, thus initiating the phagocytic response by activating the complement. The acute phase response develops in a wide range of acute and chronic inflammatory conditions like bacterial, viral, or fungal infections; rheumatic and other inflammatory diseases; malignancy; and tissue injury or necrosis. These conditions cause release of interleukin-6 and other cytokines that trigger the synthesis of CRP and fibrinogen by the liver. During the acute phase response, levels of CRP rapidly increase within 2 hours of acute insult, reaching a peak at 48 hours. Because there are a large number of disparate conditions that can increase CRP production, an elevated CRP level does not diagnose a specific disease. An elevated CRP level can provide support for the presence of an inflammatory disease, such as rheumatoid arthritis, polymyalgia rheumatica or giant-cell arteritis. CRP levels are also indicative of the presence of infections.

Capillarity

Capillary attraction, or capillarity, is the ability of a liquid to flow in narrow spaces without the assistance of, and in opposition to external forces like gravity. As a result of capillarity liquids can be drawn up in porous materials such as paper, in some non-porous materials such as liquified carbon fiber, or in a cell. In the present invention capillary forces result in absorption of the liquid sample in the application zone, as well as migration of the analytes contained in the sample from the application zone to the at least one detection zone.

Colloidal Metal

Colloidal metal is a suspension (or colloid) of sub-micrometre-sized particles of metal in a fluid, such as, but not limited to, water.

Any colloidal metal can be used in the present invention. Colloidal metal includes any water-insoluble metal particle or metallic compound dispersed in liquid water, a hydrosol or a metal sol. Preferred metals include gold, silver and platinum.

Conjugation

Conjugation is the process by which the colloidal metal particles are bound (conjugated) to a molecule such as a protein. One embodiment of the present invention relates to a protein, in particular an antibody, conjugated to colloidal metal particles, where the colloidal metal is a noble metal, in particular gold, silver and platinum. Conjugation can be performed by adsorption of the metal particles to the protein or antibody, or by covalent binding of the metal particles to thiol groups presented by the protein or antibody.

Detection Zone

The term detection zone refers to the part of the device in which concentration of an analyte is determined by measuring the induced changes in electrical properties of said detection zone. In a preferred embodiment of the present invention, the detection zone is located on a strip consisting of or comprising blotting paper and a membrane. The detection zone comprises molecules which are immobilised and which are capable of binding specifically the analyte of interest. Migration of the analytes contained in the sample and applied to the application zone through the detection zone allows binding of this specific molecule to the analyte. The analyte specifically bound by the immobilised molecule conjugated to the reporter is thus retained in the detection zone. The detection zone can be subdivided in several detection zones, each containing a specific immobilised molecule which can be different from or identical to the immobilised molecules in any other detection zone. In one embodiment, at least one of the detection zones contains immobilised bovine serum albumin (BSA). In another embodiment, at least one of the detection zones contains a positive control. The detection zone is such that impedance and/or capacitance can be measured with electrodes. The induced changes in electrical properties measured in the detection zone varies as a function of the amount of metal particles retained in said detection zone.

Disease or Medical Condition

The terms disease or medical condition are to be construed as referring to any pathological disorder in a body (animal or plant organism). Of particular interest for the present invention are infections, including bacterial, viral and fungal infections, chronic diseases and medical conditions that can last for a long time, such as inflammation, such as, but not limited to, inflammation in patients having undergone orthopaedic surgery such as implantation of an artificial member such as a hip, inflammation in patients having undergone implantation surgery such as implantation of an artificial cardiac valve, inflammation in patients suffering from arthritis, cancer, autoimmune diseases. Biological markers (analytes) of such diseases can be monitored by patient operated equipment such as the device or system of the present invention and can therefore be part of telemedical treatment. Particularly conditions which require regular or repeated monitoring at a medical examiner's practice or at a point-of-care are of interest. Any disease or medical condition for which a biological marker is known is relevant.

Electrical Impedance

Electrical impedance is the measure of the resistance that a circuit presents to the passage of a current when a voltage is applied. In quantitative terms, it is the complex ratio of the voltage to the current in an alternating current (AC) circuit. Impedance extends the concept of resistance to AC circuits, and possesses both magnitude and phase, unlike resistance, which has only magnitude. In direct current (DC) circuits, there is no distinction between impedance and resistance; the latter can be thought of as impedance with zero phase angle. It is necessary to introduce the concept of impedance in AC circuits because there are other mechanisms impeding the flow of current besides the normal resistance of DC circuits. There are an additional two impeding mechanisms to be taken into account in AC circuits: the induction of voltages in conductors self-induced by the magnetic fields of currents (inductance), and the electrostatic storage of charge induced by voltages between conductors (capacitance). The impedance caused by these two effects is collectively referred to as reactance and forms the imaginary part of complex impedance whereas resistance forms the real part. Measurement of impedance requires measurement of the magnitude of voltage and current, and the phase difference between them. The symbol for impedance is Z and impedance is expressed in ohms ($\Omega$).

Electrodes

An electrode is an electrical conductor used to make contact with a non-metallic part of a circuit. Electrodes are herein used to make contact between the reader unit and the detection zones. The term electrode refers to both contact and non-contact electrodes. Capacitive electrodes do not require an ohmic connection to the electrolyte (detection zone) and therefore the capacitive electrodes are also called non-contact electrodes. The capacitive electrode is a conductor coated with an electrical insulating layer. There is no conduction between the electrode and the electrolyte (detection zone). Thus, the capacitive electrodes are not in direct contact with the molecules in the detection zone.

The impedance electrodes have an ohmic connection, i.e. a direct contact to the electrolyte (detection zone).

In one embodiment, the impedance matching of the electrodes is achieved by coating the electrodes with a salt such as silver chloride. Embodiments of the present invention relate to devices in which the impedance of the detection zones is measured with at least two electrodes. In one embodiment, two electrodes are used for measuring impedance in at least two detection zones; the electrodes are moved relative to the device so that they can be contacted sequentially with each detection zone. In another embodiment, two electrodes are used for measuring impedance in each detection zone; in this embodiment, the number of electrodes is the double of the number of detection zones, and the impedances of each detection zone can be measured simultaneously. In a preferred embodiment, the impedance of each detection zone is measured with three electrodes. In another preferred embodiment, the impedance of each detection zone is measured with four electrodes.

Liquid Sample

The term liquid sample is to be understood as any sample in the liquid form, containing analytes. Preferred embodiments are those in which the liquid sample is a bodily sample, such as a urine sample, a blood sample, an interstitial fluid sample, or a plant sample. Preferably, the sample originates from a human. The volume of the sample is such that migration of the analytes contained in the sample from the application zone to the detection zone is possible; in particular the analytes shall be capable of migrating at least until beyond the last detection zone. In one embodiment the volume of the sample is less that 50 microliter ($\mu L$), in a preferred embodiment the volume of the sample is in the interval from 5 $\mu L$ to 10 $\mu L$.

Membrane

A membrane in the context of the present invention is a carrier such as a nitrocellulose, a polyvinylidene fluoride (PVDF) or a nylon membrane, or any membrane known in the art, to which molecules such as antibodies can be immobilised.

Metal

The term "metal" as used herein is an element, compound, or alloy that is a good conductor of both electricity and heat, which readily loses electrons to form positive ions (cations), and that belongs to the "metal" group as known in the state of the art and as defined by its position on the periodic table. Of particular relevance for the present invention are metal particles which can be conjugated to antibodies.

Noble Metal

The noble metals are metals that are resistant to corrosion and oxidation in moist air, unlike most base metals, even at high temperatures. The grouping is not strictly defined but usually is considered to include rhenium, ruthenium, rhodium, palladium, silver, osmium, iridium, platinum, and gold; i.e., the metals of groups VIIb, VIII, and Ib of the second and third transition series of the periodic table.

Paper Chromatography

Paper chromatography is a separation technique. In the present context, paper chromatography is the process by which the analytes contained in the sample applied to the application zone migrate to the at least one detection zones.

Reader Unit

A reader unit is any device capable of assessing the impedance spectrum measured in the at least one detection zone by the at least two electrodes. Preferably, the reader unit comprises a display unit, which displays the impedance spectrum of the detection zone. More preferably, the reader unit is calibrated in such a way that it can display the concentration of the analyte of interest, converted from the impedance spectrum measured in the detection zone. The reader unit can be connected to a power source, a printer unit, and is connected to the at least two electrodes. In a preferred embodiment the reader unit is powered with batteries and is portable. The reader unit may comprise a data storage unit and/or a data transmission unit.

Rheumatoid Factor (RF)

Rheumatoid factor (RF) is the autoantibody (antibody directed against an organism's own tissues) that is most relevant in rheumatoid arthritis (RA). RA is an autoimmune disease and a form of inflammatory arthritis. RA is a chronic disease. Evidence shows that early diagnosis, early treatment, and aggressive treatment to put the disease into remission are the best means of avoiding joint destruction, organ damage and disability. The causes of RA remain unknown, but are likely a combination of genetic and environmental factors.

RF is an antibody against the Fc portion of IgG. It is used as a biological marker of RA and Sjögren's syndrome. The presence of RF in the serum is not proof in itself that the tested subject suffers from RA or Sjögren's syndrome. Instead, its presence has to be interpreted in conjunction with other symptoms in order to make a clear diagnosis. Elevated levels of RF can also be associated with other autoimmune activity, such as tissue or organ rejection RF levels are also a good indicator of the intensity of diseases and can help determine whether treatment is required.

Sensors

The sensors as used herein is capable of measuring impedance changes over a single frequency, impedance changes over a range of frequencies (impedance spectrum), changes in capacitance and/or resonant frequency in the detection zone. The measurable changes in the detection zone can be active (induced) or passive. The measurable changes can be induced by applying a frequency stimulus signal through the detection zone. Impedance and/or capacitance changes are then captured based on the changes induced in the detection zone. When the measurable changes are passive, a magnetic field of an approaching or stationary object may in one embodiment impact resonant frequency of detection electrodes. In another embodiment, the permeability of a material may impact the impedance of the detection electrodes. The measurements made by the sensor can be used to deduce an impedance spectrum.

Strip

The term "strip" as used herein comprises a blotting paper and a membrane suitable for immobilizing molecules, such as antibodies. It is preferred that the strip comprises at least one application zone and at least one detection zone. In a preferred embodiment the strip comprises at least one application zone, at least one migration zone and at least one detection zone. Within the scope of the invention are embodiments in which the blotting paper is any paper known in the art as being suitable for blotting procedures, and in which the membrane is selected from the group consisting of polyvinylidene fluoride (PVDF), nitrocellulose and nylon membranes. Other membranes suitable for immobilising molecules such as the specific molecules B are also envisioned. In a preferred embodiment the device as described herein is a strip.

Systemic Lupus Erythematosus (SLE)

Systemic lupus erythematosus (SLE or lupus) is a systemic autoimmune disease that can affect any part of the body. SLE most often harms the heart, joints, skin, lungs, blood coagulation system, blood vessels, liver, kidneys, and nervous system. The course of the disease is unpredictable, with periods of illness (called flares) alternating with remissions. There is no cure for SLE, which can be fatal. Current treatments involve steroids, which are known for having strong, undesirable side-effects, and should thus be administered as little as possible.

Antinuclear antibody (ANA) testing and anti-extractable nuclear antigen (anti-ENA) form the mainstay of serologic testing for SLE. In particular, anti-dsDNA is a known hallmark of SLE.

Tumor Factor p53 p53 (also known as protein 53 or tumor protein 53), is a tumor suppressor protein that in humans is encoded by the TP53 gene. p53 is crucial in multicellular organisms, where it regulates the cell cycle and, thus, functions as a tumor suppressor that is involved in preventing cancer. As such, p53 has been described as "the guardian of the genome" because of its role in conserving stability by preventing genome mutation. The p53 tumor suppressor is a sequence-specific transcription factor and acts as a central hub sensing various stress signals and activating an array of target genes to induce cell cycle arrest, apoptosis, and senescence. In response to various stress signals such as DNA damage, hypoxia, or activated oncogenes, the p53 protein is activated in a specific manner by posttranslational modifications and leads to DNA repair, cell cycle arrest, apoptosis, or cellular senescence. Alteration of the p53 gene is the most frequent genetic alteration in human cancer, and it leads to the accumulation of mutant p53 in the nucleus of tumor cells. Anti-p53 antibodies can be found in the serum of patients with various cancer types. Moreover, a good correlation exists between the presence of anti-p53 antibodies and the presence of a mutation in the p53 gene. The presence of antibodies against p53 is associated with poor disease outcome. Antibodies against p53 were found more frequently in advanced tumor stages. Thus monitoring p53 antibody concentration is relevant for monitoring the progress of various cancer types and for evaluating responsiveness to treatment and/or therapy such as chemotherapy.

DETAILED DESCRIPTION OF THE INVENTION

The present invention relates to a device for measuring the concentration of analytes in a liquid sample by measuring variations in impedance and/or capacitance in a detection zone. The said device is particularly useful for determining the concentration of biological markers in bodily samples, such as blood, urine or interstitial fluid samples, wherein the said biological markers are characteristic of a bacterial, viral or fungal infection or of a chronic disease or condition, or the severity thereof. The device does not require any laboratory setting, and as such is particularly useful for point-of-care or home monitoring.

The device is divided in at least two zones: at least one application zone and at least one detection zone. In a preferred embodiment, a strip made of blotting paper and a membrane suitable for immobilizing molecules, such as antibodies, comprise the at least one application zone and the at least one detection zone. In a preferred embodiment, the at least one application zone is one application zone. The application zone contains free molecules A that are capable of binding specifically the analyte C of interest, said molecules A being conjugated to a reporter D which is such that variations in the amount of reporter molecules result in induced changes in electrical properties. Each of the at least one detection zones is such that a molecule B, which is capable of binding the analyte C specifically, is immobilised to its surface. In one preferred embodiment, the device comprises a stripas defined herein. The molecule B is immobilised to the surface of the membrane. Methods of immobilisation for attaching the specific molecules B to the membrane are methods known by the skilled user, and include methods of affinity binding and covalent binding.

The specific molecules A and B within the scope of the present invention are such that the specific molecule A and the specific molecule B are different from each other or identical to each other, provided they can bind specifically to the same analyte C simultaneously. Molecules A and B can be antibodies, including monoclonal antibodies, polyclonal antibodies, bispecific antibodies. In one embodiment, molecule A is a monoclonal antibody and molecule B is a polyclonal antibody. In another embodiment, molecule A is a polyclonal antibody and molecule B is a monoclonal antibody. In yet another embodiment, molecule A and molecule B are different monoclonal antibodies. In another embodiment, molecule A and molecule B are different polyclonal antibodies. Or, molecule A and molecule B are the same bispecific antibody.

Within the scope of the present invention are embodiments in which the analyte C specifically bound by A and B is a biological marker, preferably a biological marker for a bacterial, viral or fungal infection, for a disease or a medical condition or for the severity thereof, even more preferably a chronic disease or condition. The analyte C can be any component, substance or biochemical constituent. This includes macromolecules comprised in liquid samples, including bodily samples such as blood samples, urine samples or interstitial fluid sample. In one embodiment the bodily samples originate from mammalian organisms, such as humans, cattle or pets. In other embodiments, the samples originate from fish or farm animals such as poultry, In yet another embodiment, the samples originate from a plant. Such macromolecules can be, but are not limited to, antigens, proteins, peptides, polysaccharides, oligosaccharides, hormones, growth hormones. Of particular interest for the present invention are analytes which can be bound specifically by at least one molecule such as the specific molecules A or B as described above. In some embodiments, the analyte C is a biological marker for inflammation, for infections, for cancer or for rheumatoid arthritis; these markers include CRP, p53, anti-dsDNA antibodies and rheumatoid factor.

Upon application of the sample to the application zone, the analyte C is bound by the specific molecule A conjugated to the reporter D (hereinafter referred to as AD complex). The analytes contained in the sample, including the analyte C, migrate via capillary forces from the application zone to the at least one detection zone. Each detection zone carries immobilised molecules B, which are capable of binding the analyte C specifically regardless of whether the analyte C is already bound by the specific molecule A. When the analyte C, bound to AD, migrates through the detection zone on the surface of which the specific molecule B is immobilised, the analyte C is retained in the detection zone upon specific binding by the immobilised molecule B. The analytes that are not bound specifically by the molecule B migrate beyond the detection zone. In a preferred embodiment the molecule B is bound directly to the strip. It is preferred that B is not bound to the electrode.

The detection zone now presents on its surface complexes ADC consisting of: specific molecule A conjugated to reporter D and bound to analyte C, which is also bound by specific molecule B immobilised in the detection zone. The reporter D is a reporter which is able to yield a change in changes in electrical properties such as the impedance and/or capacitance. The impedance and/or capacitance of the detection zone is thus dependent on the amount of reporter D.

In one embodiment, the reporter D is a colloidal metal, preferably a noble metal such as, but not limited to, gold, silver, iridium, platinum, osmium, rhodium, palladium and ruthenium colloids. Preferred embodiments are gold, silver and platinum. The metal particles can be conjugated to the specific molecules A by methods known in the art, such as adsorption or covalent binding, for example covalent binding to thiol groups present on the specific molecule A.

The device can be adapted so that it comprises several detection zones, each suitable for the detection of a specific analyte. This can be useful to increase sensitivity, if several biological markers are characteristic of a pathological condition when present in combination. Such a device also allows diagnosis of several conditions simultaneously. In one embodiment, the detection zone consists of at least two detection zones, such as at least three detection zones, such as at least four detection zones, such as at least five detection zones. Thus in one embodiment the detection zone consists of five detection zones.

In one embodiment, one of the detection zones is a negative control on which a molecule E, which does not bind any of the analytes C of interest, is immobilised. In one embodiment the molecule E is bovine serum albumin (BSA). The variations in impedance and/or capacitance measured in the negative control zone result from unspecific binding of analytes to the molecule E and are used as reference. In such an embodiment, the impedance $\Delta Z$ of the at least one detection zone is determined as being the difference between the impedance $Z_d$ of the at least one detection zone and the impedance $Z_n$ of the at least one control zone, such that the impedance Z is given by the formula: $\Delta Z = Z_d - Z_c$; $Z_c$ is control or the impedance due to the background noise. Alternatively, the variation in impedance ΔZ of the at least one detection zone is determined as being the ratio between the impedance $Z_d$ of the at least one detection zone and the impedance $Z_c$ of the at least one control zone, such that the impedance Z is given by the formula: $\Delta Z=Z_d/Z_c$. In one embodiment the concentration of the at least one analyte C is determined for each of the at least one of the detection zones as a function of impedance ΔZ.

In another embodiment the capacitance of the at least one detection zone is determined as being the difference or the ratio between the capacitance $C_d$ of the at least one detection zone and the capacitance $C_c$ of the at least one negative control zone, such that the capacitance C is given by the formula: $\Delta C=C_d-C_c$ or $\Delta C=C_d/C_c$. In one embodiment the concentration of the at least one analyte C is determined for each of the at least one of the detection zones as a function of capacitance ΔC.

In another embodiment, one of the detection zones is a positive control on which a molecule F has been immobilised. This positive control zone is preferably located at the end of the strip that is located farthest from the application zone, and may contain a visual assay indicating that migration proceeded properly. Thus it is possible to ascertain that enough sample volume was applied to the application zone, or that no impurities prevented proper migration of the analytes through the whole of the device. The molecule F can be any molecule capable of binding to a compound known to be present in the application zone or in the liquid sample. In a preferred embodiment, the molecule F is an antibody against one of the specific molecules A conjugated to the reporter D. In another embodiment, the molecule F is an antibody against one of the analytes known to always be present in the bodily sample, for example if the sample originates from a human, the molecule F is an antibody directed against constant regions of human antibodies. Thus, provided that F is capable of binding AD specifically via specific binding to A, the only requirement for accumulation of reporter D in the positive control zone is that the AD complex migrated from the application zone to the detection zone. In one embodiment, proper migration can be verified by a visual assay. For example, the reporter D can be colloidal gold, which can precipitate and give rise to a visible signal in the positive control zone, as is well known in the art. In another embodiment, the impedance and/or capacitance of the positive control zone is measured in order to verify proper migration.

In yet another embodiment, the device contains a positive control zone, a negative control zone, and at least one detection zone, such as at least two detection zones, such as at least three detection zones, such as at least four detection zones, such as at least five detection zones. In a particular embodiment, the device comprises a positive control zone, a negative control zone and five detection zones.

In another embodiment, the device can be housed in a housing to prevent external agents such as dust particles to gather on the strip and interfere with the analysis. The housing can consist of a plastic casing, or any casings known in the art.

In one embodiment, the device is used for monitoring analytes that are biological markers for infections, diseases or disorders, or the severity thereof. Diseases or disorders that can be monitored are: inflammation and certain forms of auto-immune disorders, including inflammation following orthopaedic surgery, inflammation due to rejection of an artificial implant such as a hip or a cardiac valve; certain types of cancer, more particularly cancers in which anti-p53 antibodies are produced in the body; rheumatoid arthritis; polymyalgia rheumatic; lupus erythrodematosis disseminates; inflammatory response or bacterial, viral or fungal infection after transplantation or implantation. In one embodiment, the device is used for measuring the concentration of at least two analytes, such as at least three analytes, such as at least four analytes, such at least five analytes.

It is an object of the present invention to provide a method for measuring the concentration of at least one analyte C in a liquid sample. In one embodiment, the method comprises applying a liquid sample to the application zone of the device, the application zone comprising at least one molecule A capable of binding specifically to the analyte C and being coupled to a reporter D. In another embodiment the liquid sample is added to a reservoir comprising a buffer. Buffer comprising sample is then applied to the application zone, for example by dipping or immersing the part of the strip comprising the application zone into the buffer in the reservoir. In an embodiment A is in the Buffer. The buffer can for example be an isotonic buffer and/or comprise detergents such as Tween20.

The complex consisting of the molecule A and the reporter D is not immobilised to the surface of the application zone. Upon application of the sample, the analyte C is bound by the molecule A, resulting in a complex ADC consisting of C, A and D. The analytes migrate from the application zone to the detection zone, said detection zone comprising at least one molecule B capable of binding specifically to said analyte C, in which the molecule B is immobilised on the surface of the detection zone and the molecule A and the molecule B can bind the analyte C simultaneously. Upon migration of the analytes through the detection zone, the molecule B will retain the complexes ADC by binding the analyte C. The impedance and/or capacitance in the at least one detection zone is measured, and is optionally compared to the impedance and/or capacitance of another detection zone on which no reporter D is bound.

Migration of the analytes from the application zone to the at least one detection zone is the result of capillary forces or paper chromatography.

Also within the scope of the present invention is a method in which the application zone contains a set of molecules $A_k$ that each specifically bind an analyte $C_m$, and in which each of the at least one detection zone i contains an immobilised molecule $B_i$ different from any molecule $B_j$ present in any other detection zone j, where i, j, k and m are integers. Thus in one embodiment, $1<i<5$, $1<j<5$, $1<k<5$ and $1<m<5$. In another embodiment, the application zone contains 5 molecules A (coupled to a reporter D): $A_1$, $A_2$, $A_3$, $A_4$ and $A_5$, each binding an analyte $C_1$, $C_2$, $C_3$, $C_4$ or $C_5$; the device comprises 5 detection zones, each with a molecule $B_1$, $B_2$, $B_3$, $B_4$ or $B_5$ immobilised to the surface, where each of the molecules $B_1$, $B_2$, $B_3$, $B_4$ or $B_5$ is different from the B molecule present in any other detection zone. Upon migration $A_1$ is bound by $B_1$, $A_2$ is bound by $B_2$, $A_3$ is bound by $B_3$, $A_4$ is bound by $B_4$ and $A_5$ is bound by $B_5$. The reporters D to which the molecules $A_k$ can be conjugated to can be identical or different.

It is an object of the present invention to monitor the concentration of analytes contained in liquid samples, in particular bodily samples, including but not limited to blood samples, urine samples and interstitial fluid samples. Embodiments within the scope of the present invention concern the monitoring of the concentration of more than one analyte, such as at least two analytes, such as at least three analytes, such as at least four analytes, such as at least five analytes. A preferred embodiment enables measurement of the concentration of two analytes. In yet another preferred embodiment one of the analytes to be monitored is always found in the liquid sample, so that measuring the impedance and/or capacitance in the detection zone in which this analyte is retained enables a positive control ensuring that the migration of the analytes has occurred properly. In one embodiment, the variation of impedance and/or capacitance in the positive control zone allows a visual assessment, for example by a colorimetric reaction such as known in the art. One of the detection zones can be a negative control zone, on which a molecule is immobilised which does not specifically bind any of the analytes of interest. Measuring the impedance and/or capacitance of this negative control zone yields a measure of the background noise impedance, to be subtracted from the impedance and/or capacitance measured in the other detection zones.

The impedance and/or capacitance of the detection zones is measured using a set of at least two electrodes connected to a power source. In one embodiment, the electrodes are impedance-matched to the reporter D. In another embodiment, the electrodes are impedance-matched to the at least one detection zone. Embodiments in which the change in impedance and/or capacitance is measured by at least two electrodes, such as at least three electrodes, such as at least four electrodes, such as at least five electrodes, such as at least six electrodes, are also within the scope of the invention. In a one embodiment the impedance and/or capacitance is measured with two electrodes. In a preferred embodiment the at least two electrodes are impedance electrodes or capacitive electrodes. The impedance changes and/or changes in capacitance may also be monitored using two impedance electrodes and capacitive electrodes.

The electrodes used in the context of the present invention are manufactured from a metal, preferably selected from the group of noble metals. Preferred embodiments include electrodes manufactured from a noble metal selected from the group of gold, silver, platinum, iridium, osmium, rhodium and ruthenium, or alloys thereof. Preferred embodiments are gold, silver and platinum. The electrodes, connected to a power source, and the at least one detection zone and can be set in movement relative to one another. In one preferred embodiment the electrode is an impedance electrode or a capacitive electrode. In another preferred embodiment both electrodes are comprised in the device. The use of impedance and/or capacitive electrodes results in more specific measurements of the concentration of analyte.

A preferred embodiment of the present invention relates to a device containing at least two detection zones. When two electrodes are used, the impedances and/or capacitances of the at least two detection zones can be measured sequentially. In the embodiments in which more than two electrodes are used, the impedances and/or capacitances of the at least two detection zones can be measured simultaneously or sequentially; in a preferred embodiment the impedances and/or capacitances of the at least two detection zones are measured simultaneously.

The present invention also relates to a system for measuring the concentration of at least one analyte in a liquid sample, said system comprising the device of the present invention, a reader unit into which the device can be inserted, at least two electrodes capable of measuring the impedance and/or capacitance of the at least one detection zone, a power source and a data output. In one embodiment the electrodes are comprised in the reader unit. The at least two electrodes are in a preferred embodiment impedance electrodes or capacitive electrodes. The system or reader unit may for example comprise at least two impedance electrodes and at least two capacitive electrodes. The system showed in FIG. 6 comprises two detection zones, 4 capacitive electrodes and eight impedance electrodes. In one embodiment, the system further comprises a sensor capable of measuring impedance changes over a single frequency, impedance changes over a range of frequencies, changes in capacitance and/or resonant frequency in the detection zone. The sensor is defined elsewhere herein. The sensor is in one embodiment comprised in the reader.

In an essential embodiment at least the part of the device which contains the at least one detection zone can be inserted in the reader. A reader unit comprising a temperature sensor is also within the scope of the present invention. In one embodiment, the reader unit is connected to a power source, such as batteries or a power generator. The reader unit can comprise a data storage unit and can be connected to a printer unit. The reader unit can also comprise a user interface and a display unit which can display the concentration of the analytes retained in the at least one detection zone. In one embodiment, the system can measure the concentration of at least two analytes in a liquid sample, such as at least three analytes, such as at least four analytes, such as at least five analytes.

The device of the present invention is easy to operate and thus particularly well suited for home-monitoring. It is expected that using the device of the present invention will yield economic benefits for society, as it will be cheaper to use than the currently available tests that can only be performed in laboratory settings such as a medical practice, and thus require trained operators such as laboratory technicians or nurses. It is also expected that the present device will result in limited consultations, which often prove to be unnecessary after they have been performed.

The present device is also well suited for point-of-care diagnosis and monitoring of disease progression or response to a treatment. It can for example be used for diagnosis in ambulances, thus allowing a faster and cheaper diagnosis than if the patient had to be driven to the hospital for examination.

DETAILED DESCRIPTION OF DRAWINGS

Figure 1:
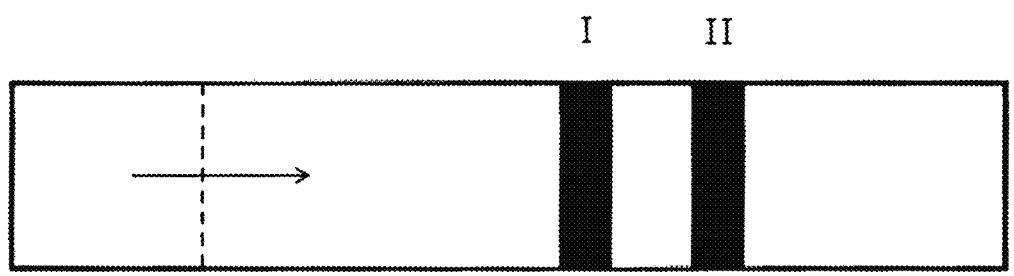
FIG. 1 shows a schematic, simplified view of an embodiment of the device.

FIG. 1 shows a schematic, simplified view of an embodiment of the device. A strip with an application zone (to the left of the dotted line) and two detection zones I and II (to the right of the dotted line). The arrow represents the direction of migration (from left to right).

Figure 2:
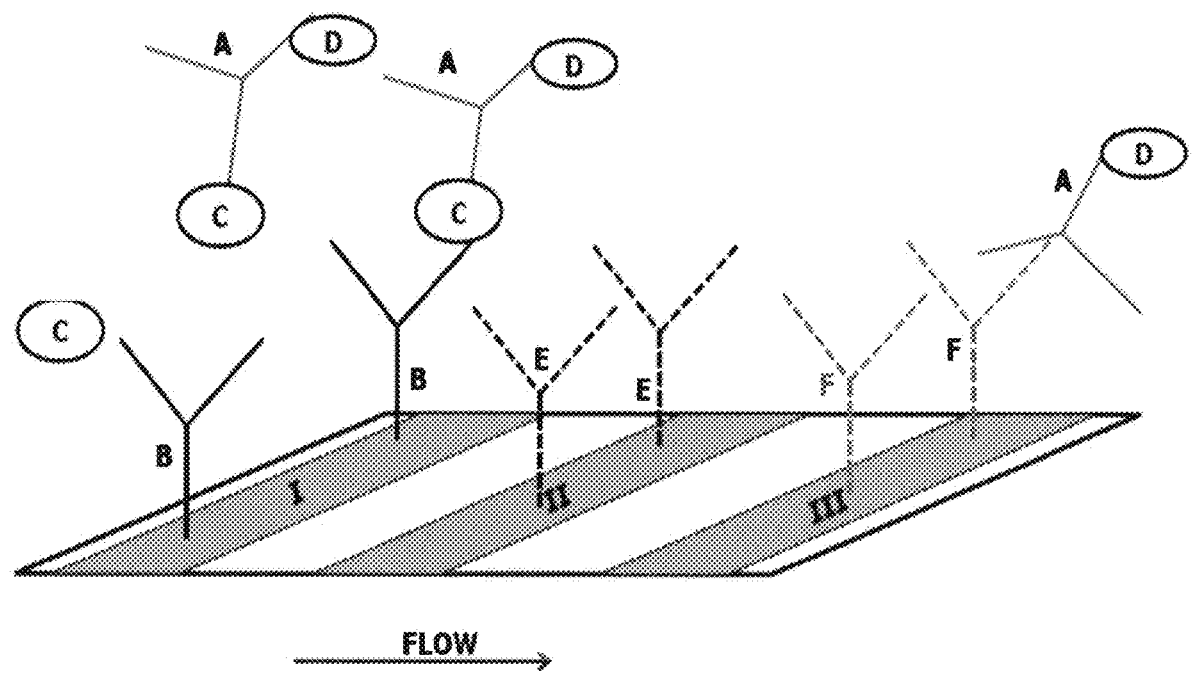
FIG. 2 shows a detailed schematic view of an embodiment of the device.

FIG. 2 shows a detailed schematic view of an embodiment of the present invention. In the application zone (not shown), the analyte C is bound specifically by molecule A conjugated to reporter D. The strip in this case presents three detection zones (I, II and III in dark grey). Specific molecule B, which is capable of binding specifically the analyte C, is immobilised on the surface of detection zone I. Upon migration, B binds the ADC complex, which is retained in zone I. Molecule E is a negative control immobilised on the surface of detection zone II, and does not bind AD or C. Molecule F is a positive control capable of binding specific molecule A conjugated to D. The arrow shows the direction of migration.

Figure 3:
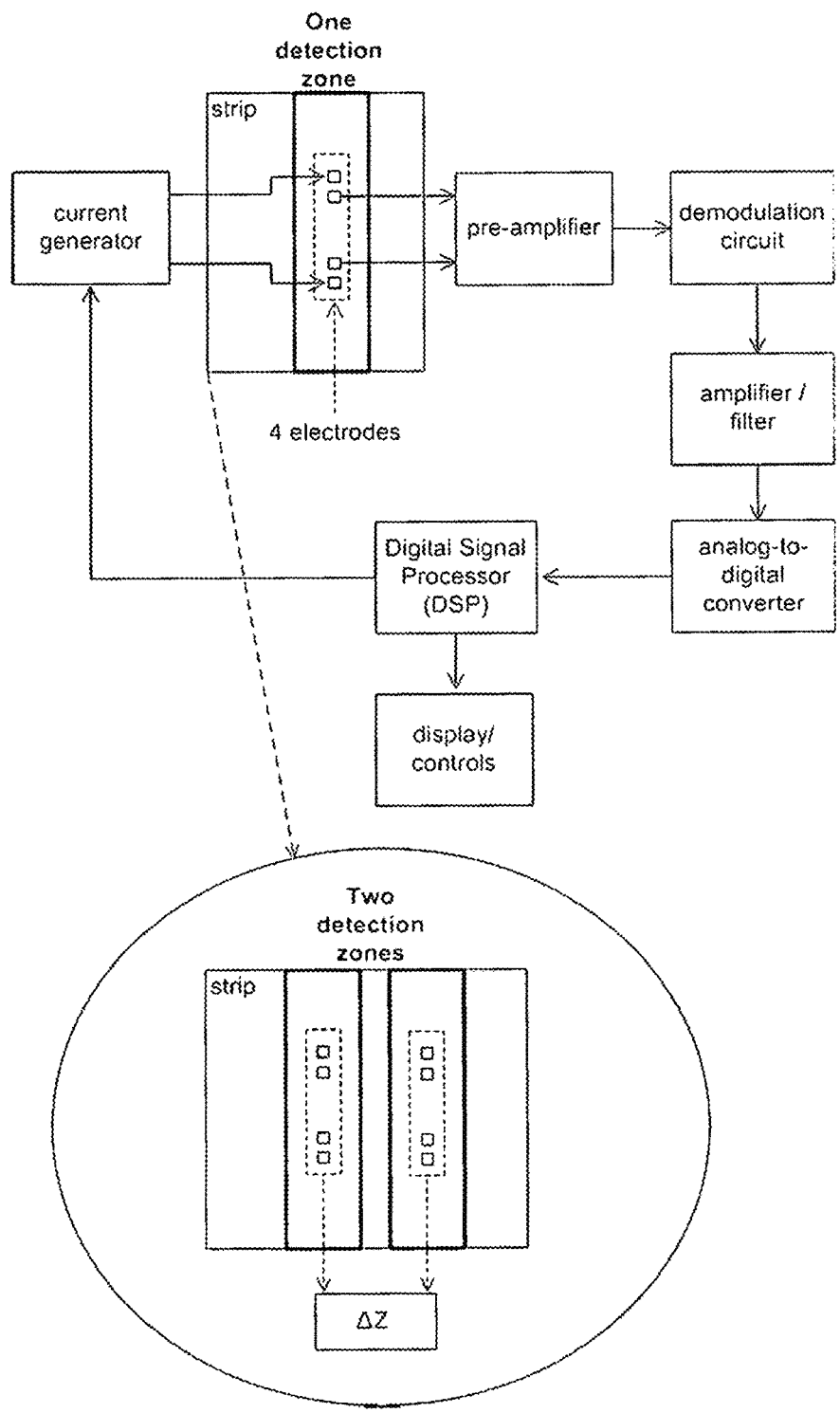
FIG. 3 shows a schematic representation of how to perform measurements.

FIG. 3 shows a flow-chart representation of a possible embodiment of the system, with either one or two detection zones. ΔZ: variation in impedance.

Figure 4:
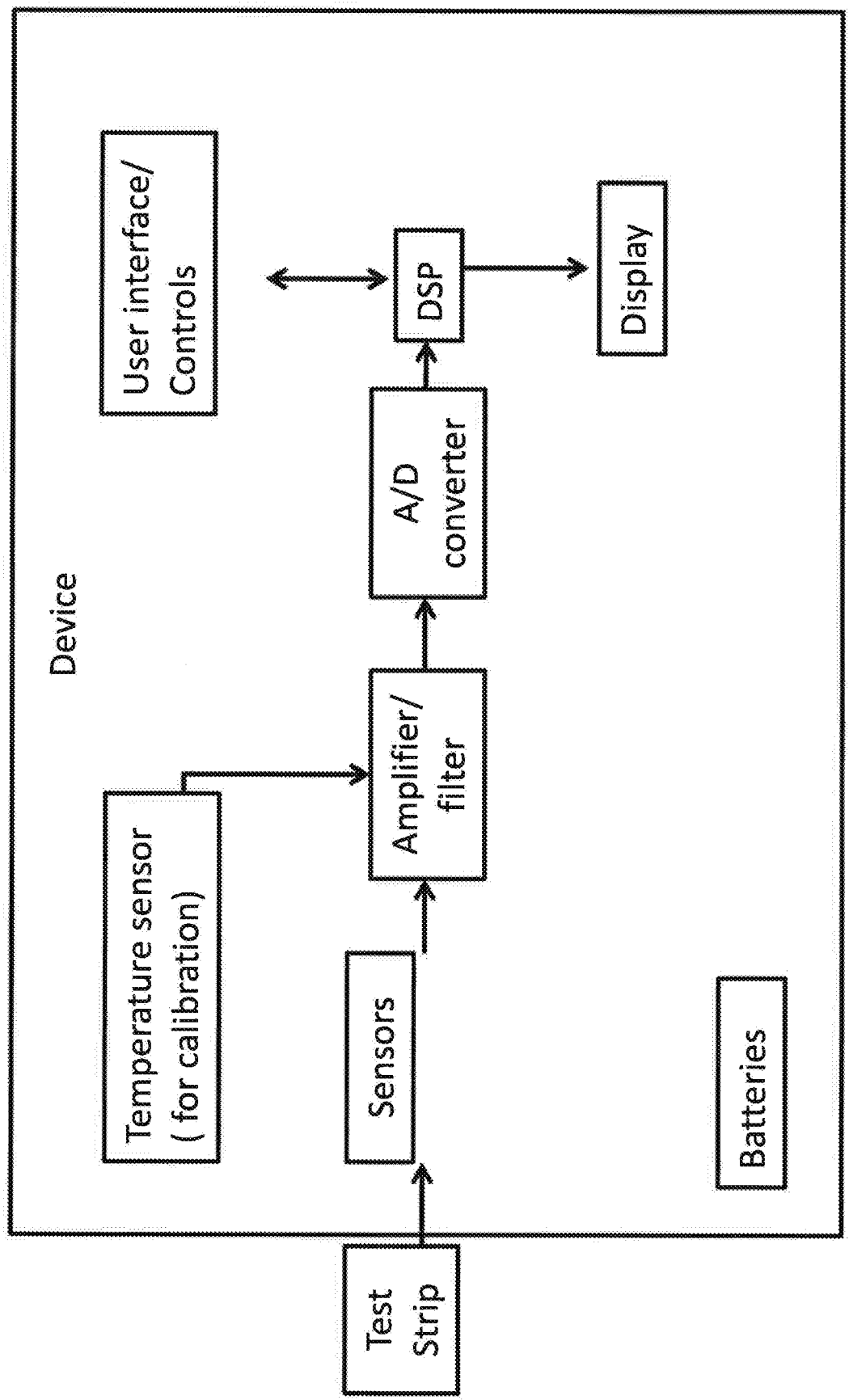
FIG. 4 is a schematic diagram of a possible embodiment of the system.

FIG. 4 is a schematic diagram of a possible embodiment of the system. Here a strip is introduced into a system comprising batteries, electrochemical or optical sensors, a temperature sensor, an amplifier/filter, an A/D converter, a DSP (digital signal processing) unit, a display unit and user interface.

Figure 5:
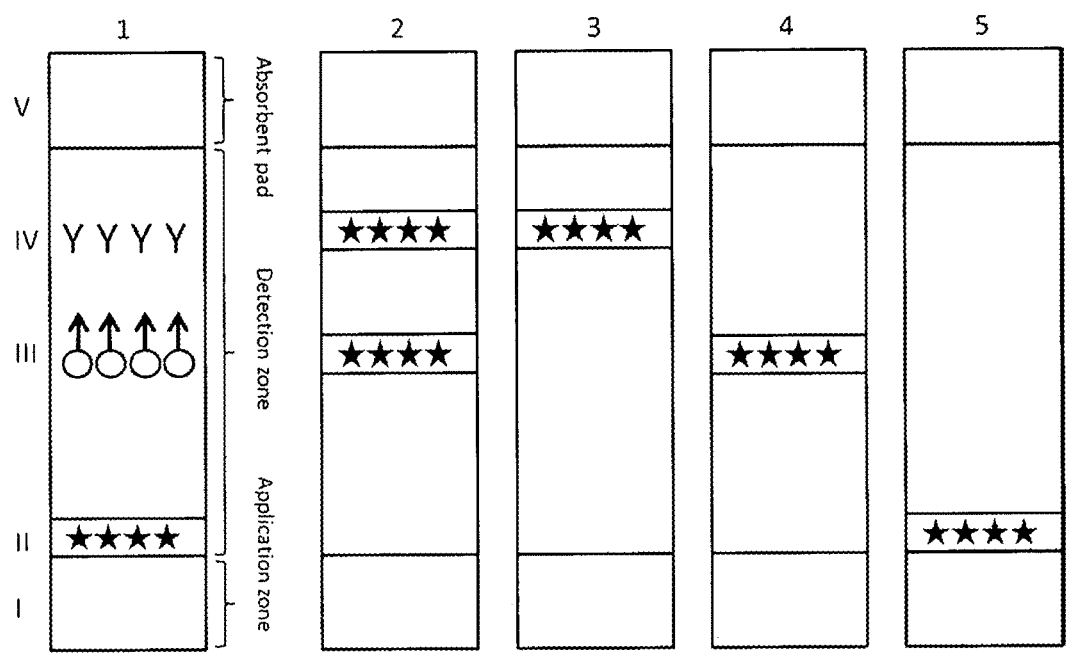
FIG. 5 is a schematic representation of an embodiment of the device and 4 possible outcomes.

FIG. 5 is a schematic representation of an embodiment of the device and 4 possible outcomes. (1) shows the different zones of the strip. (I) is the sample pad (application zone) to which the sample containing the analytes C is applied; (II) is a conjugate pad, comprising the specific molecule A linked to the reporter D. This is where the analyte C is bound by AD to form the complex ADC. (III) is the first detection zone, on which the specific molecule B is immobilized. (IV) is the second detection zone, in this example the positive control zone, on which a molecule F (which binds to the molecule A in this example) is immobilised. (V) is an absorbent pad.

(2), (3), (4) and (5) show different possible outcomes. (2) The complex ADC is retained in III via binding of C to the specific molecule B. The complex AD in excess (not bound to C) is likewise retained in IV via binding of A to the positive control molecule F. This test is valid and positive. (3) The complex ADC is not retained in III via binding of C to the specific molecule B. The complex AD is retained in IV via binding of A to the positive control molecule F. This test is valid and negative. (4) The complex ADC is retained in III via binding of C to the specific molecule B. The complex AD is not retained in IV via binding of A to the positive control molecule F. This test is not valid. (5) The complex ADC is not retained in III via binding of C to the specific molecule B. The complex AD is not retained in IV via binding of A to the positive control molecule F. The AD and ADC complexes did not migrate and are still in the application zone. This test is not valid.

Figure 6:
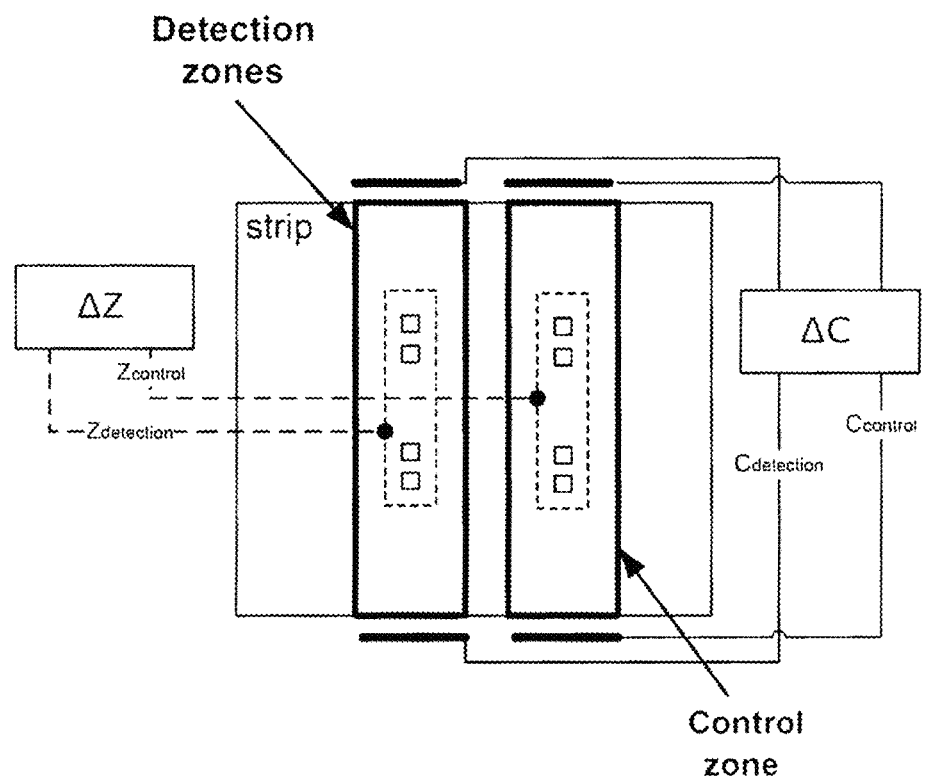
FIG. 6 is a schematic representation of an embodiment of the system.

FIG. 6 is a schematic representation of an embodiment of the system. The figure show a part of a strip having a detection zone and a control zone. The detection zone and the control zone each have four impedance electrodes (squares). Two capacitive electrode (bold lines) are located outside the detection zone and two capacitive electrode (bold lines) are located outside the control zone. ΔZ is the change in impedance: $\Delta Z = Z_{detection} - Z_{control}$. ΔC is the change in capacitance: $\Delta C = C_{detection} - C_{control}$.

Items

The following items shall not be construed as claims.

Item 1: A device for measuring the concentration on an analyte in a liquid sample by measuring the induced changes in electrical properties, said device consisting of:

at least one application zone allowing application of a liquid sample, the application zone comprising at least one molecule A capable of binding specifically to an analyte C, said at least one specific molecule A being coupled to a reporter D, said at least one molecule A not being immobilised on the surface of the application zone, and wherein said reporter D is capable of affecting impedance and/or capacitance;

at least one detection zone comprising at least one molecule B capable of binding specifically to said analyte C, said at least one molecule B being immobilised on the surface of the at least one detection zone, wherein the at least one specific molecule A and the at least one specific molecule B can bind the analyte C simultaneously; and in which the application zone and the at least one detection zone are connected such that the analytes contained in the liquid sample applied to the application zone can migrate from the application zone to the at least one detection zone.

Item 2: The device according to item 1, in which the molecules A and B, which are capable of binding specifically to the analyte C, are antibodies.

Item 3: The device according to any of the preceding items, in which the molecules A and/or B, which are capable of binding specifically to the analyte C, are polyclonal antibodies.

Item 4: The device according to any of the preceding items, in which the molecules A and/or B, which are capable of binding specifically to the analyte C, are monoclonal antibodies.

Item 5: The device according to any of the preceding items, in which one of the molecules A and B, which are capable of binding specifically to the analyte C, is a polyclonal antibody, and the other one of the molecules A and B is a monoclonal antibody.

Item 6: The device according to any of the preceding items, in which the analyte C is a biological marker.

Item 7: The device according to item 6, in which the analyte C is a biological marker for a bacterial, viral or fungal infection, for a disease or a medical condition or for the severity or activity of a disease or a medical condition.

Item 8: The device according to item 7, in which the analyte C is a biological marker for a disease or a medical condition selected from the group of: bacterial, viral or fungal infections, inflammation, cancer, autoimmune diseases such as arthritis, rheumatism, polymyalgia rheumatica, systemic lupus erythematosus (SLE), inflammatory response or bacterial, viral or fungal infection after transplantation or implantation.

Item 9: The device according to any of items 6 to 8, in which the analyte C is an antigen.

Item 10: The device according to any of items 6 to 9, in which the analyte C is a protein.

Item 11: The device according to item 10, in which the analyte C is a protein selected from the group consisting of C-reactive protein CRP, tumor protein 53, rheumatoid factor, anti-dsDNA antibodies.

Item 12: The device according to any of the preceding items, in which the reporter D is a metal.

Item 13: The device according to item 12, in which the reporter D is a colloidal metal particle or a non-colloidal metal particle.

Item 14: The device according to any of items 12 to 13, in which the colloidal metal particle is a noble metal particle or a combination of noble metal particles.

Item 15: The device according to item 14, in which the noble metal is selected from the group consisting of gold, silver, platinum.

Item 16: The device according to item 15, in which the noble metal is gold.

Item 17: The device according to any of the preceding items, in which the reporter D is coupled to the at least one specific molecule A by adsorption or by covalent binding.

Item 18: The device according to any of the preceding items, in which the application zone to which the sample is applied consists of a container.

Item 19: The device according to any of items 1 to 17, in which the application zone consists of a strip.

Item 20: The device according to item 19, in which the strip comprises blotting paper and a membrane.

Item 21: The device according to any of the preceding items, in which the at least one detection zone consists of a strip.

Item 22: The device according to item 21, in which the strip consists of blotting paper in contact with a membrane on which the at least one specific molecule B is bound.

Item 23: The device according to item 22, wherein the at least one specific molecule B is immobilized on the membrane of the at least one detection zone by one of the following methods: affinity binding, covalent binding.

Item 24: The device according to any of items 22 to 23, in which the membrane is selected from the group of polyvinylidene fluoride (PVDF) membranes, nitrocellulose membranes and nylon membranes.

Item 25: The device according to any of the preceding items, in which the at least one detection zone is divided in at least two detection zones, such as at least three detection zones, such as at least four detection zones, such as at least five detection zones.

Item 26: The device according to item 25, in which each detection zone i contains an immobilized molecule $B_i$ different from the immobilized molecule $B_j$ present in any other detection zone j, where i and j are integers.

Item 27: The device according to item 26, in which the application zone contains a number of specific molecules $A_k$, in which k is an integer.

Item 28: The device according to item 27, in which each of the specific molecules $A_k$ is coupled to identical or different reporters D.

Item 29: The device according to item 28, in which at least one of the detection zones is a negative control zone, on which a molecule E is immobilised which does not capable of binding any of the analytes C, of the reporters D, of the specific molecules A or of the specific molecules B.

Item 30: The device according to item 29, in which there are at least two negative control zones.

Item 31: The device according to any of items 29 to 30, in which there are two negative control zones.

Item 32: The device according to item 31, in which the two negative control zones are not adjacent.

Item 33: The device according to item 28, in which one of the detection zones allows a positive control to ensure that proper migration of the analytes between the application and the detection zone occurred.

Item 34: The device according to item 33, in which a molecule F is immobilised on the surface of the positive control zone, said molecule F being capable of binding at least one of the at least one specific molecule A, said at least one specific molecule A being bound to the reporter D.

Item 35: The device according to item 33, in which the detection zone comprising the positive control is the detection zone farthest from the application zone.

Item 36: The device according to any of the preceding items, in which the device is contained in a housing that prevents spillage of the liquid sample and contamination by external agents.

Item 37: A method for measuring the concentration of at least one analyte C in a liquid sample, said method consisting of:
  i) applying a liquid sample to an the application zone the application zone comprising at least one molecule A capable of binding specifically to an analyte C, said at least one specific molecule A being coupled to a reporter D, said at least one molecule A not being immobilised on the surface of the application zone, so that analyte C from the sample is bound by the at least one specific molecule A conjugated to the reporter D;
  ii) allowing migration of the analytes contained in the application zone to a detection zone comprising at least one molecule B capable of binding specifically to said analyte C, said at least one molecule B being immobilised on the surface of the at least one detection zone, wherein the at least one specific molecule A and the at least one specific molecule B can bind the analyte C simultaneously;
  iii) wherein the at least one immobilised molecule B capable of binding specifically the analyte C will retain the analyte C conjugated to the reporter D;
  iv) measuring the impedance and/or capacitance in the at least one detection zone; and
  v) optionally comparing the impedance and/or capacitance of the detection zone to the impedance and/or capacitance in another detection zone without reporter D.

Item 38: The method according to item 37, in which migration of the analytes is the result of capillarity or paper chromatography.

Item 39: The method according to any of items 37 to 38, in which the application zone of the device contains a set of molecules $A_k$ that each specifically binds an analyte $C_m$, and in which the at least one detection zone of the device each contains an immobilized molecule $B_i$ different from the immobilized molecule $B_j$ present in any other detection zone j, where i, j, k and m are integers.

Item 40: The method according to any of items 37 to 39, in which the liquid sample is a bodily sample isolated from an organism selected from the group consisting of humans, farm animals, pets and plants.

Item 41: The method according to any of items 37 to 40, in which the bodily sample is selected from the group consisting of blood sample, interstitial fluid sample and urine sample.

Item 42: The method according to any of items 37 to 41, in which the liquid sample is a blood sample.

Item 43: The method according to any of items 37 to 42, in which the concentration of more than one analyte is measured, such as the concentration of at least two analytes, at least three analytes, at least four analytes, at least five analytes.

Item 44: The method according to any of items 37 to 43, in which the concentration of two analytes is measured.

Item 45: The method according to any of items 37 to 44, in which the change in impedance and/or capacitance is measured by a set of at least two electrodes, such as a set of two electrodes, three electrodes, four electrodes.

Item 46: The method according to any of items 37 to 45, in which the change in impedance and/or capacitance is measured by a set of four electrodes.

Item 47: The method according to any of items 37 to 46, in which the change in impedance and/or capacitance is measured by a set of three electrodes.

Item 48: The method according to any of items 37 to 45, in which the change in impedance and/or capacitance is measured by a set of two electrodes.

Item 49: The method according to any of items 37 to 48, in which the electrodes are manufactured from a metal.

Item 50: The method according to any of items 37 to 49, in which the electrodes are manufactured from a metal selected from the group of noble metals.

Item 51: The method according to any of items 37 to 50, in which the electrodes are manufactured from a noble metal selected from the group of gold, silver, platinum, iridium, platinum, osmium, rhodium and ruthenium, or an alloy thereof.

Item 52: The method according to any of items 37 to 51, in which the electrodes are manufactured from gold.

Item 53: The method according to any of items 37 to 52, in which the electrodes are impedance-matched to the reporter D.

Item 54: The method according to any of items 37 to 52, in which the electrodes are impedance-matched to the detection zones.

Item 55: The method according to any of items 37 to 54, in which there are at least two detection zones, such as at least three detection zones, such as at least four detection zones, such as at least five detection zones.

Item 56: The method according to item 55, in which the impedances of the at least two detection zones are measured simultaneously.

Item 57: The method according to item 55, in which the impedances of the at least two detection zones are measured sequentially.

Item 58: The method according to any of items 55 to 57, in which at least one of the detection zones is a negative control zone, on which a molecule E is immobilised, which specifically binds analytes not to be found in the liquid sample.

Item 59: The method according to item 58, in which the impedance Z of the at least one detection zone is determined as being the difference or the ratio between the impedance $Z_d$ of the at least one detection zone and the impedance $Z_n$ of the at least one negative control zone, such that: $Z=Z_d-Z_n$ or $Z=Z_d/Z_n$.

Item 60: The method according to item 59, in which the concentration of the at least one analyte C is determined for each of the at least one of the detection zones as a function of impedance Z.

Item 61: A system for measuring the concentration of at least one analyte in a liquid sample, said system comprising
the device according to any of items 1 to 37,
a reader unit for inserting said device,
a set of at least two electrodes capable of measuring the impedance and/or capacitance of the at least one detection zone,
a power source, and
a data output.

Item 62: The system according to item 61, in which the electrodes are comprised in a reader unit.

Item 63: The system according to any of items 61 to 62, in which at least the part of the device containing the at least one detection zone can be inserted into the reader unit.

Item 64: The system according to any of items 61 to 63, in which the reader unit contains a temperature sensor.

Item 65: The system according to any of items 61 to 64, in which the system comprises a user interface.

Item 66: The system according to any of items 61 to 65, adapted to measure the concentration of more than one analyte, such as the concentration of at least two analytes, at least three analytes, at least four analytes, at least five analytes.

Item 67: The system according to any of items 61 to 66, adapted to measure the concentration of two analytes.

Item 68: The system according to any of items 61 to 67, in which the device and the set of at least two electrodes can be moved relative to one another.

Item 69: The system according to any of items 61 to 68, in which the system comprises a display unit.

Item 70: The system according to item 69, in which the system displays the concentration of the analyte present in the detection zone to which the electrodes are connected.

Item 71: The system according to any of items 61 to 70, in which power is provided from batteries.

Item 72: The system according to any of items 61 to 71, in which the system is portable.

Item 73: The system according to item 72, in which the system is handheld.

Item 74: The system according to any of items 61 to 72, in which the system comprises means for wireless data communication.

Item 75: Use of a system according to any of items 61 to 74 for determining the concentration of at least one analyte in a liquid sample.

The invention claimed is:

1. A device for measuring the concentration of an analyte in a liquid sample by measuring the induced changes in electrical properties, said device comprising:
at least one application zone allowing application of a liquid sample, the application zone comprising at least one molecule A capable of binding specifically to an analyte C, said at least one specific molecule A being coupled to a reporter D, said at least one molecule A not being immobilised on the surface of the application zone, and wherein said reporter D is capable of affecting electrical properties;
at least one detection zone comprising at least one molecule B capable of binding specifically to said analyte C, said at least one molecule B being immobilised on the surface of the at least one detection zone, wherein the at least one specific molecule A and the at least one specific molecule B can bind the analyte C simultaneously and wherein said detection zone is in ohmic contact with at least two electrodes; and
in which the application zone and the at least one detection zone are connected such that the analytes contained in the liquid sample applied to the application zone can migrate from the application zone to the at least one detection zone, wherein an increase in the concentration of reporter-conjugated molecules in the detection zone induces detectable changes in the impedance of the detection zone that can be measured with said electrodes in ohmic contact with the detection zone and configured to provide direct electrical contact with the liquid sample.

2. The device according to claim 1, in which the molecules A and B are antibodies.

3. The device according to claim 1, in which the analyte C is C-reactive protein CRP, tumor protein 53, rheumatoid factor, or anti-dsDNA antibodies, and/or in which the reporter D is a colloidal metal particle or a non-colloidal metal particle.

4. The device according to claim 3, wherein the colloidal metal particle is a noble metal particle or a combination of noble metal particles.

5. The device of claim 4, wherein the noble metal is selected from the group consisting of gold, silver, and platinum.

6. The device of claim 1, wherein the application and detection zones are present on a strip.

7. The device of claim 6, wherein the strip is made from a membrane.

8. The device of claim 7, wherein the membrane is made from polyvinylidene fluoride (PVDF), nitrocellulose, or nylon.

9. The device of claim 1, being contained in a housing.

10. A system for measuring the concentration of at least one analyte in a liquid sample, said system comprising
the device according to claim 1,
a reader unit for inserting said device,
a power source, and a data output.

11. The system according to claim 10, further comprising a second set of at least two electrodes capable of measuring the impedance and/or capacitance of the at least one detection zone.

12. The system according to claim 11, wherein the second set of at least two electrodes are impedance electrodes or capacitive electrodes.

13. The system according to claim 11 comprising at least two impedance electrodes and at least two capacitive electrodes.

14. The system according to claim 10 further comprising a sensor capable of measuring impedance changes over a single frequency, impedance changes over a range of frequencies, changes in capacitance and/or resonant frequency in the detection zone.

15. The system of claim 10, further comprising a user interface.

16. The system of claim 10, further comprising a display.

17. The system of claim 10, configured for wireless communication.

* * * * *